(12) United States Patent
Jones et al.

(10) Patent No.: US 7,883,526 B2
(45) Date of Patent: *Feb. 8, 2011

(54) EMBOLIC COIL HAVING STRETCH RESISTANT MEMBER WITH AN ATTACHED END AND AN END WITH MOVEMENT FREEDOM

(75) Inventors: Donald K. Jones, Dripping Springs, TX (US); Vladimir Mitelberg, Austin, TX (US); William W. Sowers, Pembroke Pines, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 656 days.

This patent is subject to a terminal disclaimer.

(21) Appl. No.: 11/678,351

(22) Filed: Feb. 23, 2007

(65) Prior Publication Data
US 2008/0086163 A1   Apr. 10, 2008

Related U.S. Application Data

(63) Continuation-in-part of application No. 11/539,937, filed on Oct. 10, 2006.

(51) Int. Cl.
*A61M 29/00* (2006.01)
(52) U.S. Cl. .................. 606/200; 606/191; 623/23.76
(58) Field of Classification Search ........... 606/200; 623/1.15, 23.76
See application file for complete search history.

(56) References Cited

U.S. PATENT DOCUMENTS

| | | |
|---|---|---|
| 5,217,484 A | 6/1993 | Marks |
| 5,261,916 A | 11/1993 | Engelson |
| 5,304,195 A | 4/1994 | Twyford, Jr. et al. |
| 5,582,619 A | 12/1996 | Ken |
| 5,833,705 A | 11/1998 | Ken et al. |
| 5,853,418 A | 12/1998 | Ken et al. |
| 6,004,338 A | 12/1999 | Ken et al. |
| 6,013,084 A | 1/2000 | Ken et al. |

(Continued)

FOREIGN PATENT DOCUMENTS

WO    WO 2006/032291 A1    3/2006

OTHER PUBLICATIONS

European Search Report dated Dec. 12, 2007 for European Application No. EP 07 25 3738.

*Primary Examiner*—(Jackie) Tan-Uyen T Ho
*Assistant Examiner*—Julie A Szpira
(74) *Attorney, Agent, or Firm*—Cook Alex Ltd.

(57) ABSTRACT

A coil device is provided with a stretch resistant feature. The device includes a wound coil defining a lumen and a stretch resistant member at least partially received within the lumen. A headpiece is formed by a joining of the coil and a restrictor member, typically by plasma welding. The restrictor member is also at least partially received within the lumen and defines an aperture adapted to movably receive a portion of the stretch resistant member to allow the wound coil to stretch and elongate. The stretch resistant member includes an enlarged portion that is larger than the aperture and adapted to engage the restrictor member to prevent or resist stretching of the wound coil. The restrictor member may be provided as a separate element fixedly secured to the coil wire, or the coil wire may include one or more minor turns adapted to perform the function of the restrictor member.

17 Claims, 2 Drawing Sheets

U.S. PATENT DOCUMENTS

| | | |
|---|---|---|
| 6,063,100 A | 5/2000 | Diaz et al. |
| 6,117,157 A * | 9/2000 | Tekulve ................. 606/200 |
| 6,179,857 B1 | 1/2001 | Diaz et al. |
| 6,183,491 B1 * | 2/2001 | Lulo ..................... 606/191 |
| 6,193,728 B1 | 2/2001 | Ken et al. |
| 6,551,340 B1 | 4/2003 | Konya et al. |
| 6,616,617 B1 * | 9/2003 | Ferrera et al. ........... 600/585 |
| 2003/0014073 A1 * | 1/2003 | Bashiri et al. ........... 606/200 |
| 2003/0120302 A1 * | 6/2003 | Minck et al. ............ 606/200 |
| 2004/0002733 A1 * | 1/2004 | Teoh ..................... 606/200 |
| 2004/0034378 A1 * | 2/2004 | Monstadt et al. ........ 606/157 |
| 2005/0043755 A1 | 2/2005 | Wilson et al. |
| 2006/0079926 A1 | 4/2006 | Desai et al. |

* cited by examiner

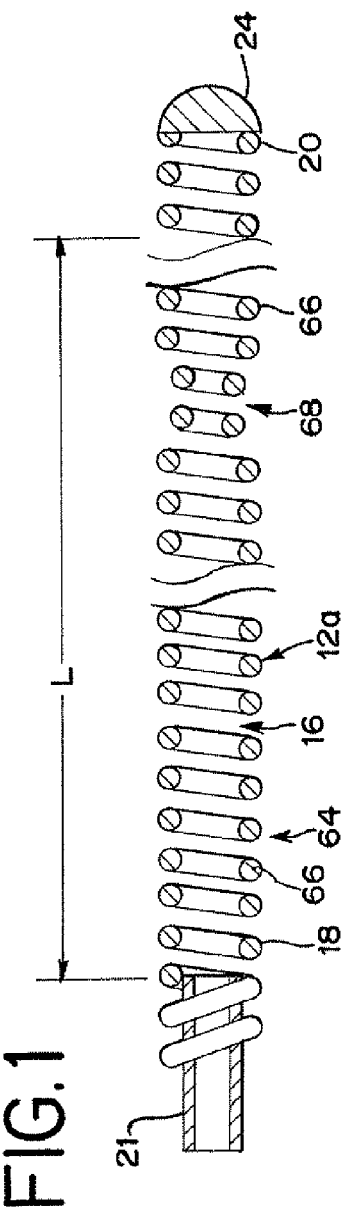
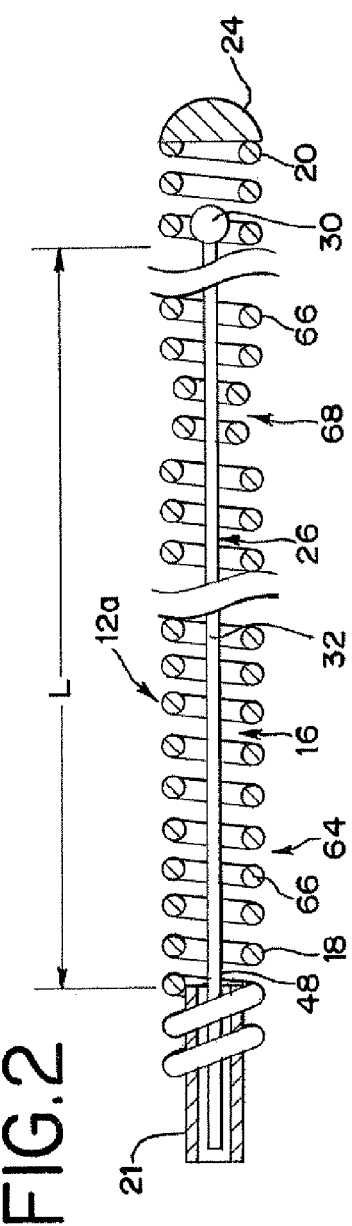
FIG.1
FIG.2

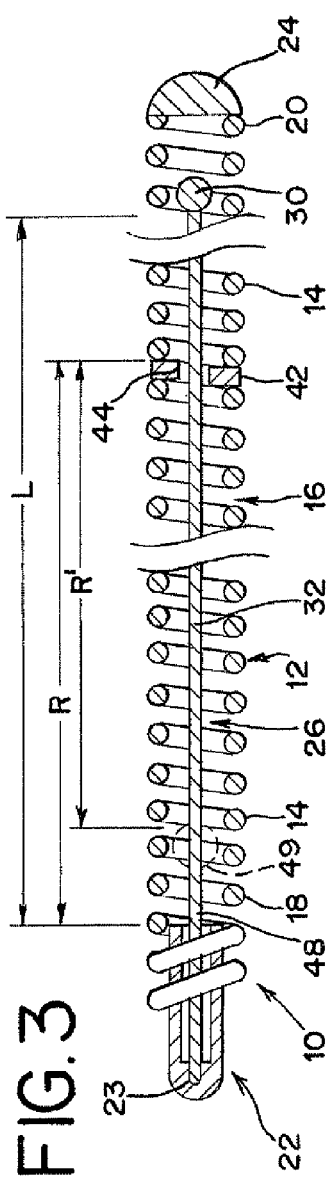
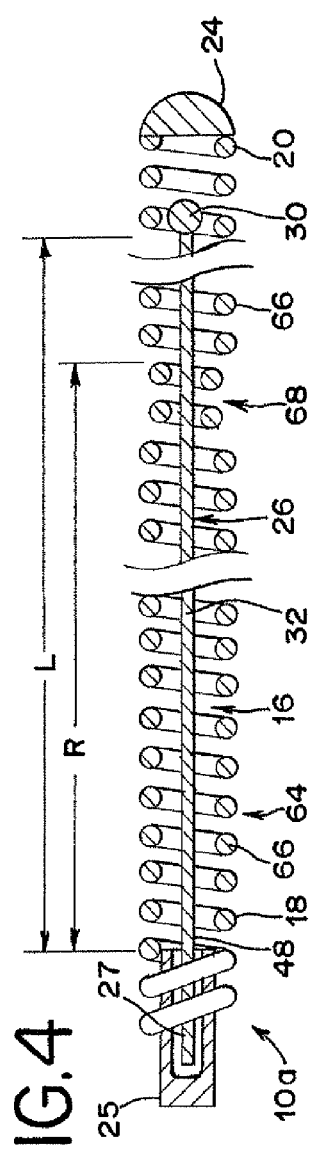
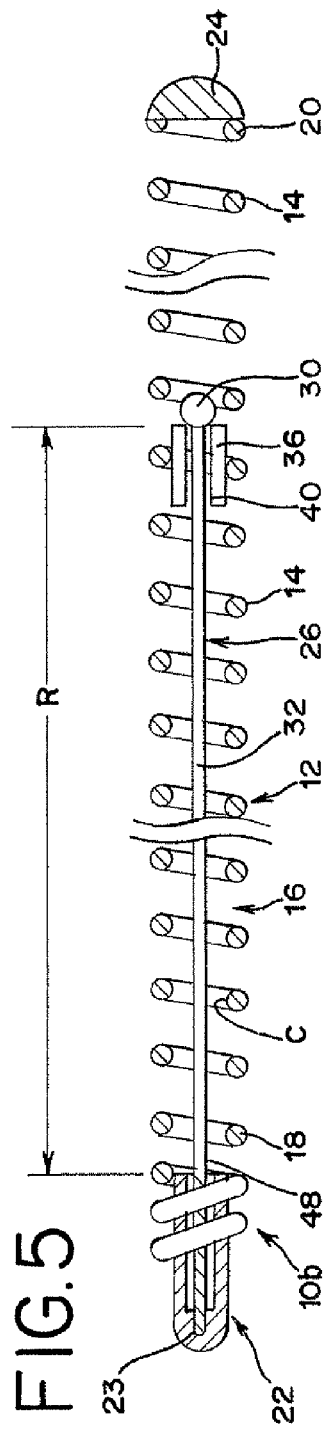

EMBOLIC COIL HAVING STRETCH RESISTANT MEMBER WITH AN ATTACHED END AND AN END WITH MOVEMENT FREEDOM

CROSS REFERENCE TO RELATED APPLICATION

This is a continuation-in-part of application Ser. No. 11/539,937, filed Oct. 10, 2006, which is hereby incorporated herein by reference.

FIELD OF THE INVENTION

This invention generally relates to medical devices implantable within body vessels and vessel defects of a human subject. More particularly, this invention relates to embolic coils having a stretch resistant feature exhibiting an end connection that has freedom of movement.

DESCRIPTION OF RELATED ART

The use of embolic coils in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site, such as an aneurysm. A vascular occlusion device, such as an embolic coil, is attached to the end of a delivery member, which pushes the coil through the catheter and out of the distal end of the catheter into the delivery site. A multiplicity of coils can be packed within the aneurysm to limit or prevent blood flow thereinto. Some of the problems that have been associated with these procedures relate to stretching of the embolic coils. For example, a stretched coil may exhibit diminished pushability and/or retractability. Furthermore, an overly stretched coil will occupy less volume than a relaxed or un-stretched coil, thereby occupying less space within an aneurysm, which increases the number of coils required to sufficiently pack the aneurysm and prevent blood flow thereinto.

In response to these concerns, devices have been developed in an attempt to provide a coil that will resist stretching. One such device is disclosed in U.S. Pat. No. 5,582,619 to Ken, which is hereby incorporated herein by reference. The coils described in Ken include an elongated stretch-resisting member received within the lumen of the coil and fixed at each end of the coil. The stretch-resisting member prevents excessive stretching, but may adversely affect the flexibility of the coil because it extends along the entire length of the coil. It is important for embolic coils to be flexible, because they must adapt to the shape of the target site and any other previously placed coils.

One approach to the flexibility concerns associated with the Ken coils is described in U.S. Pat. No. 6,183,491 to Lulo, which is hereby incorporated herein by reference. Lulo provides a coil with a support wire fixedly attached to a proximal end of the coil and to an intermediate portion of the coil, proximal to the distal end of the coil. Hence, the Lulo coil is proposed for preventing stretching of the turns of the coil between the ends of the support wire by tightly securing them to each other. However, it may be desirable to allow for some limited stretching of the turns of the coil between the ends of the support wire for increased flexibility.

Therefore, a need remains for an embolic coil having an optimal combination of stretch resistance and flexibility. It has come to be appreciated in conjunction with the present invention that distal end flexibility can result in especially advantageous operation and properties.

SUMMARY OF THE INVENTION

According to an embodiment or aspect of the present disclosure, an embolic coil is provided with a wound coil having a plurality of turns defining a lumen. A headpiece is positioned at the proximal portion of the wound coil and an endcap is positioned at the distal portion of the wound coil. The embolic coil further includes a stretch resistant member at least partially received within the lumen and having an anchored proximal end portion, a distal end portion, an enlarged portion. The anchored portion is fixedly attached to the wound coil and the headpiece. A restrictor member is at least partially received within the lumen, and a location along the lumen, such as at the restrictor member, defines an aperture smaller than the enlarged portion of the stretch resistant member. A portion of the stretch resistant member is movable through the aperture to allow freedom of movement between the wound coil and the stretch resistant member. This includes stretching of the wound coil until the enlarged portion engages the restrictor member to resist further stretching of the wound coil.

According to another embodiment or aspect of the present disclosure, an embolic coil is provided with a wound coil having a plurality of major turns defining a lumen. The embolic coil further includes a stretch resistant member at least partially received within the lumen and having an anchored proximal end portion, a distal end portion, and an enlarged portion. A minor turn of wound coil defines an aperture smaller than the enlarged portion of the stretch resistant member to define a restrictor member. A portion of the stretch resistant member is movable through the aperture to allow freedom of movement between the wound coil and the stretch resistant member. This includes stretching of the wound coil until the enlarged portion engages the minor turn and resists further stretching of the wound coil. The proximal portion of the stretch resistant member is fixedly attached to the wound coil and a headpiece to provide a proximally anchored stretch resistant member.

BRIEF DESCRIPTION OF THE DRAWINGS

FIG. 1 is a partial cross-sectional view of components positioned as an intermediate assembly for making an embolic coil according to an aspect of the present invention;

FIG. 2 is a partial cross-sectional view of components, including those assembled according to FIG. 1, used in forming an embolic coil according to this aspect of the invention;

FIG. 3 is a partial cross-sectional view of an embolic coil having a stretch resistant member proximally anchored according to an aspect of the present invention;

FIG. 4 is a partial cross-sectional view of components positioned as an assembly that is an alternative to the assembly of FIG. 2 for making an embolic coil according to an aspect of the present invention; and FIG. 5 is a partial cross-sectional view of another embodiment of an embolic coil having a stretch resistant member with a free-floating distal end portion and an anchored proximal end portion.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIGS. 1 and 2 illustrate formation of an embolic coil according to an aspect of the present invention. A wound coil 12a comprised of a plurality of turns defining a central lumen 16 is positioned for assembly. The wound coil 12a is illustrated as a substantially uniform helical coil having an aperture area of reduced diameter, but may take virtually any form, such as a coil having a varying pitch or random shape configuration and/or a coil that is substantially uniform along its length. The wound coil may be comprised of any material, but it may be preferred to use a radiopaque material, such as platinum, or to at least provide the wound coil with a radiopaque layer or markers to improve traceability within a body vessel. The wound coil 12 that is illustrated in FIG. 3 extends from a proximal coil portion 18 to a distal coil portion 20 and, in the illustrated embodiment, is bounded by a headpiece 22 positioned at the proximal portion 18 and an endcap 24 positioned at the distal portion 20.

The assembly of this illustrated proximal end portion is exemplified in FIGS. 1 and 2, and the headpiece 22 is formed from a hypotube 21. The wound coil is secured to the hypotube 21 in a manner that can vary depending on the materials used for each, but suitable means may include plasma welding, welding, soldering, crimping, adhesion, bonding, and press fitting, each in accordance with practices, equipment and materials generally known in the art. As noted in the following disclosure, plasma welding typically is used in a subsequent operation illustrated in FIG. 2, and this assembly of the hypotube to the coil can proceed during the same operation.

With further reference to FIG. 2, a stretch resistant member 26, described in more detail herein, is shown in position to be secured to the assembly of FIG. 1. More specifically, the proximal end portion of the stretch resistant member 26 is positioned within the hypotube 21 to a location such as shown in FIG. 2. Thereafter, the assembly of FIG. 2 is subjected to assembly treatment, usually under plasma welding conditions according to procedures and using equipment as generally known in the art. Typical plasma welding includes use of a torch-lice element that provides quick burst or pulse of gas and a low-level flame to achieve material flow and joining effects upon cooling. A typical headpiece structure that is formed by this plasma welding approach is illustrated in FIG. 3 as the headpiece 22. Headpiece 22 includes a thus formed bead 23, which typically is rounded and can be generally hemispherical as illustrated.

Bead 23 is formed with material flow between the proximal end of the stretch resistant member 26 and the hypotube 21. FIG. 3 shows same as distinct components for illustrative purposes, but it will be understood the precise interface lines that are shown in FIG. 3 typically will not be as shown but instead there is substantially more material flow to form a more homogeneous bead 23 than the definite lines of demarcation that are illustrated.

FIG. 4 illustrates an embodiment of an embolic coil 10a that includes proximal end portion formed from an intermediate assembly different from that of FIG. 2. In this embodiment, a shaped headpiece member 25 other than a hypotube is the component that is joined to the proximal end portion of the stretch resistant member 26. After the relative positioning of components that is shown in FIG. 4, plasma welding is used to flow the headpiece member 25 and stretch resistant member 26 together to provide the headpiece of this embodiment (not shown) that can have virtually the same external appearance as headpiece 22 of FIG. 3. The headpiece member 25 is solid except that it had been cut away or had been formed with a hollow portion or opening, such as illustrated longitudinal opening 27, to accommodate the proximal end of the stretch resistant member prior to the plasma welding.

The endcap 24 at the distal end may be rounded or generally hemispherical to provide the embolic coil 10 with a relatively atraumatic tip that prevents the device from puncturing a body vessel or target site during and after delivery. The headpiece 22 is adapted to interact with a delivery device, such as a catheter, during deployment of the embolic coil 10 to a target site, so the structure can vary according to the nature of the delivery device. The stretch resistant member 26 is at least partially received within the lumen 16 of the wound coil.

The stretch resistant member 26 has a distal enlarged portion 30 joined by an elongated, filamentary intermediate portion 32. While the distal enlarged portion 30 is illustrated at the distal end of the stretch resistant member 26, it may be spaced away from the ends. The enlarged portion 30 is larger than the intermediate portion 32, but it is sized to fit within the lumen 16 of the wound coil 12 for axial movement therethrough until the wound coil 12 reaches the stretched condition of FIG. 5, taking into account the reduced diameter of the lumen 16 once the wound coil 12 begins to stretch.

The stretch resistant member 26 preferably is comprised of a relatively flexible material that is substantially non-ductile when subjected to the forces associated with stretching the wound coil 12. Suitable materials include metals, such as but not limited to stainless steel, platinum, and nitinol and other metallic alloys, and polymers such as but not limited to polyethylene terephthalate (PET) or other polyesters. It is also within the scope of the present invention to provide a composite stretch resistant member, having a polymeric intermediate portion 32 and metallic enlarged portion 30, for example. The flexibility and ductility of the stretch resistant member 26 will depend in part on the material composition, with more rigid materials, such as stainless steel and austenitic nitinol, being preferred for applications requiring less flexibility and more flexible materials, such as PET and martensitic nitinol, being preferred for applications requiring more flexibility.

The stretch resistant member 26 may be formed as a unitary piece or may be provided in multiple parts, for example with the enlarged portion 30 being separate from and joinable to the intermediate portion 32. If provided in multiple parts, the means for joining the intermediate portion 32 and the enlarged portion 30 will vary according to the materials used for each. The component parts of a metallic stretch resistant member may be joined by welding, soldering, crimping, or other known means, while the component parts of a polymeric stretch resistant member may be joined by bonding, adhesion, or other known means. Plasma welding may be used.

The total length "L" of the stretch resistant member 26 is less than the maximum stretched length of the wound coil 12 to limit the available degree of stretching, as will be described in greater detail herein. Depending on the length and material composition of the stretch resistant member 26, slack in the stretch resistant member may cause it to assume a drooped condition (not illustrated) when the embolic coil 10 is in the relaxed condition of FIG. 3, but this will not affect the operation of the device.

In the embodiment of FIG. 3 for example, the stretch resistant member 26 is movably received by an annular restrictor member 42. The restrictor member 42 is spaced from the enlarged portion 30. In the illustration of the embodiment of FIG. 5, the restrictor member 36 is generally tubular and fixedly attached to an interior circumference "c" at least one of the turns 14 of the wound coil 12. Each restrictor member defines an aperture, an elongated passageway 40 in FIG. 5, sufficiently sized to receive the stretch resistant member 26. Preferably, the restrictor members 36 or 42 are sufficiently strong to resist being crushed or otherwise deformed by the tendency of the associated turns to stretch and radially contract. Causing the restrictor member to so contact the stretch resistant member 26 may adversely affect the expected operation of the embolic coil 10.

The aperture of the restrictor member 36 is smaller than the distal enlarged portion 30. Hence, it will be seen that the stretch resistant member 26 is allowed to move axially through the lumen 16 of the coil, with the aperture (elongated passageway 40 in FIG. 5 or ring 44 in FIG. 3, for example) guiding the stretch resistant member, but movement of the enlarged portion 30 into engagement with the restrictor member such as 36 or 42, limits the range of movement between the stretch resistant member 26 and the coil turns 14.

The term "aperture" is to be construed broadly and is not limited to fully bounded openings, but to any opening adapted to allow movement of the stretch resistant member intermediate portion without allowing passage of the associated enlarged portion. For example, a C-shaped restrictor member (not illustrated) may be incorporated into embolic coils according to the present invention. Another suitable configuration is a two-piece restrictor member having an arcuate, U-shaped lower piece and an inverted U-shaped upper piece (not illustrated) in touching or spaced relationship to each other. Regardless of the specific shape of the aperture, the restrictor member is preferably adapted to prevent the stretch resistant member from escaping from the aperture, which may affect the operation of the stretch resistant member 26. As the embolic coil 10 and the stretch resistant member 26 are intended to be flexible in multiple bending planes, an aperture provided as a fully bounded opening may be preferred to eliminate the risk of disengagement in any bending condition.

The restrictor member may be, according to a configuration of FIG. 3, a generally annular restrictor member. With this configuration, embolic coils have a generally annular restrictor member 42 that is fixedly attached between adjacent turns 14 of the wound coil 12. It is also contemplated that the restrictor member 42 may be secured to only one of the turns 14, rather than two. FIG. 5 shows a restrictor member 36 having a tubular configuration and has an aperture as discussed herein. Whatever stretch resistant member is used, same includes an intermediate portion (illustrated at 32) that has a length "R" between the distal enlarged portion 30 and the anchored portion 48 by which the stretch resistant member is fixedly attached to the headpiece 22. The intermediate portion alternatively can have a length "R'" between the enlarged portion 30 and another portion of the embolic coil, such as by a connector member, illustrated at 49.

The interaction between the stretch resistant member 26 and the restrictor member or aperture regulates the stretching of the portion of the wound coil 12 between the headpiece and the restrictor member, which portion is referred to herein as the restricted portion. In particular, the embolic coil is allowed to elongate and stretch, which moves the restrictor member along the restricted portion of the stretch resistant member 26 and increases the distance therebetween. Upon sufficient stretching, the restrictor member engages the enlarged portion 30 (FIG. 5) to resist or prevent further stretching. Hence, the total distance that the restricted portion is allowed to stretch is equal to the difference between the length "L" of the stretch resistant member intermediate portion 32 and the initial distance "R" between the restrictor member 42 and the anchored portion 48.

It will be seen that the stretch resistant member 26 regulates the stretching of only the restricted portion 46, and the stretching of the remainder of the wound coil 12 is otherwise uninhibited. Therefore, the overall operation of the embolic coil depends on a number of factors, including: (1) the ratio of the length of the restricted portion 46 to the length of the entire wound coil 12, (2) the total distance that the restricted portion 46 is allowed to stretch, and (3) the position of the restricted portion 46. The free-floating stretch resistant member 26 is particularly suited to a restricted portion 46 spaced from the proximal portion 18 and distal portion 20 of the wound coil 12, but alternative stretch-resistant members may be provided to achieve a restricted portion at the proximal or distal portions of the wound coil.

The embolic coil 10 of FIG. 3 is illustrated with a generally annular restrictor member 42, but the restrictor member may take any of a number of forms, as noted in the present description, including the tubular configuration of FIG. 5. The embolic coil 10b of FIG. 5 operates similarly to the embodiment of FIG. 3, with the restricted portion (such as of length "R") of the wound coil 12 being defined by the portion between the stretch resistant member anchored portion and the restrictor member.

In particular, the embolic coil 10b is allowed to elongate and stretch, which moves the restrictor member along the intermediate portion 32 of the stretch resistant member and increases the distance between the restrictor member 42 and the anchored portion 48. Upon sufficient stretching, the restrictor member 42 engages the enlarged portion 30 to resist or prevent further stretching. Hence, the total distance that the restricted portion is allowed to stretch in this embodiment is equal to the difference between the length "L" of the stretch resistant member intermediate portion 32 and the initial distance "R" between the restrictor member 42 and the anchored portion 48.

As shown in phantom in FIG. 3, the anchored portion 48 may be fixedly attached to the wound coil 12 instead of the headpiece 22. In such an embodiment, the stretch resistant member 26 preferably includes a radially extending member 49 adapted to be welded, adhered, or otherwise fixedly secured to one or more of the coils 14 of the wound coil 12. For illustrative purposes, the radially extending member 49 is shown in FIG. 3 as a generally spherical structure, but it may be provided in any of a number of simple or complex shapes, including a cylindrical orientation or a "flower-petal" configuration with a plurality of angularly spaced radial projections. Alternatively, the wound spring 12 may be provided with at least one radially inwardly projecting member (not illustrated) adapted to be fixedly secured to the stretch resistant member 26.

While the restrictor members of FIGS. 3 and 5 are described as separate elements, the wound coil may be adapted to provide one or more restrictor member-like elements. For example, FIG. 4 illustrates an embolic coil 10a comprising a wound coil 64 having a plurality of major turns 66, corresponding generally to the coil turns 14 of FIG. 3, and at least one minor turn generally illustrated at 68. While the minor turn aperture is illustrated as comprising two turns, same also may be provided as a single turn or as more than two turns or with differing numbers of turns. The minor turn feature provides a passageway that is of reduced internal size, typically diameter, with respect to the internal size of the major turns 66.

The minor turn aperture typically can be larger than the apertures of FIGS. 3 and 5 relative to the rest of the device such as the enlarged portions, because the minor turns may stretch and elongate, thereby decreasing the size of the minor turn aperture. If the minor turn aperture is not sufficiently large, it may shrink to the point where it engages and grips the intermediate portion of the stretch resistant member, which may affect the intended operation of the stretch resistant member 26. Of course, this gripping action may be factored into the design of the embolic coil, in which case it may be considered as an auxiliary or alternative stretch resistant feature.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An embolic coil comprising:
   a wound coil including a plurality of turns defining an elongated lumen, the wound coil having a proximal end portion and a distal end portion;
   a stretch resistant member that is fixedly unattached to the wound coil while being at least partially received longitudinally within the elongated lumen and having a proximal end portion, a distal end portion, and a distally positioned enlarged portion;
   a headpiece formed from a hypotube that has an outer surface secured to the coil lumen at the proximal end portion of the wound coil, with the proximal end portion of the stretch resistant member having been plasma welded to the hypotube, whereby said headpiece comprises the hypotube and the proximal end portion of the stretch resistant member, with the proximal end portion of the wound coil being secured to the headpiece outer surface;
   a restrictor member at least partially received within and fixedly attached to the wound coil lumen, wherein the restrictor member defines an aperture smaller than the distally positioned enlarged portion of the stretch resistant member, a portion of the stretch resistant member is movable through the aperture to allow stretching of the wound coil, and the distally positioned enlarged portion is adapted to engage the restrictor member to resist stretching of the wound coil during use of the coil; and
   the wound coil lumen is larger than the distally positioned enlarged portion of the stretch resistant member whereby this enlarged portion is movable through the wound coil lumen and the wound coil extends beyond the enlarged portion of the stretch resistant member.

2. The embolic coil of claim 1, wherein said restrictor member comprises a generally tubular member fixedly attached to an interior circumference of at least one of the turns of the wound coil.

3. The embolic coil of claim 1, wherein said restrictor member comprises a generally annular member fixedly attached between adjacent turns of the wound coil.

4. The embolic coil of claim 1, wherein said stretch resistant member is substantially comprised of a metallic material.

5. The embolic coil of claim 1, wherein said stretch resistant member is substantially comprised of a polymeric material.

6. The embolic coil of claim 1, further including a connection member distal of said headpiece, and said connection member secures the coil and the stretch resistant member thereat.

7. An embolic coil comprising:
   a wound coil including a plurality of turns defining an elongated lumen, the wound coil having a proximal end portion and a distal end portion;
   a stretch resistant member that is fixedly unattached to the wound coil while being at least partially received within the elongated lumen and having a proximal end portion, a distal end portion, and a distally positioned enlarged portion;
   a headpiece positioned at a proximal portion of the wound coil, said headpiece formed from a solid member with an outer surface and an opening therein, the solid member being secured to the coil lumen at the proximal end portion of the wound coil, with the proximal end portion of the stretch resistant member being inserted within the solid member opening and plasma welded to the solid member, whereby said headpiece comprises the solid member and the proximal end portion of the stretch resistant member, with the proximal end portion of the wound coil secured to the solid member outer surface;
   an endcap positioned at a distal end portion of the wound coil;
   a restrictor member at least partially received within and fixedly attached to the lumen, wherein the restrictor member defines an aperture smaller than the enlarged portion of the stretch resistant member, a portion of the stretch resistant member is movable through the aperture to allow stretching of the wound coil, and the enlarged portion is adapted to engage the restrictor member to resist stretching of the wound coil during use of the coil; and
   the wound coil lumen is larger than the distally positioned enlarged portion of the stretch resistant member whereby this enlarged portion is movable through the wound coil lumen and the wound coil extends beyond the enlarged portion of the stretch resistant member.

8. The embolic coil of claim 7, wherein said restrictor member comprises a generally tubular member fixedly attached to an interior circumference of at least one of the turns of the wound coil.

9. The embolic coil of claim 7, wherein said restrictor member comprises a generally annular member fixedly attached between adjacent turns of the wound coil.

10. The embolic coil of claim 7, wherein said stretch resistant member is substantially comprised of a metallic material.

11. The embolic coil of claim 7, wherein said stretch resistant member is substantially comprised of a polymeric material.

12. An embolic coil comprising:

a wound coil including a plurality of major turns defining an elongated lumen, the wound coil having a proximal end portion and a distal end portion;

a stretch resistant member that is fixedly unattached to the wound coil while being at least partially received within the elongated lumen and having a proximal end portion, a distal end portion, and a distally positioned enlarged portion;

a headpiece formed from a shaped member having a longitudinal opening therein and that has an outer surface secured to the coil lumen at the proximal end portion of the wound coil, with the proximal end portion of the stretch resistant member having been inserted into the longitudinal opening and plasma welded to the shaped member, whereby said headpiece comprises the shaped member and the proximal end portion of the stretch resistant member, with the proximal end portion of the wound coil being secured to the headpiece;

the wound coil includes a minor turn defining an aperture smaller than the enlarged portion of the stretch resistant member, a portion of the stretch resistant member is movable through the aperture to allow stretching of the wound coil, and the enlarged portion is adapted to engage the minor turn to resist stretching of the wound coil during use of the coil; and the wound coil lumen is larger than the distally positioned enlarged portion of the stretch resistant member whereby this enlarged portion is movable through the wound coil lumen and the wound coil extends beyond the enlarged portion of the stretch resistant member.

13. The embolic coil of claim 12, further comprising an endcap positioned at the distal end portion of the wound coil.

14. The embolic coil of claim 13, further comprising an anchored portion of the stretch resistant member fixedly attached to the wound coil at a location proximal of said enlarged portion of the stretch resistant member.

15. The embolic coil of claim 12, wherein a portion of the stretch resistant member is movable through the aperture of the minor turn to allow stretching of the wound coil, and the enlarged portion is adapted to engage the minor turn to resist stretching of the wound coil.

16. The embolic coil of claim 12, wherein said stretch resistant member is substantially comprised of a metallic material.

17. The embolic coil of claim 12, wherein said stretch resistant member is substantially comprised of a polymeric material.

* * * * *